Figure 2:
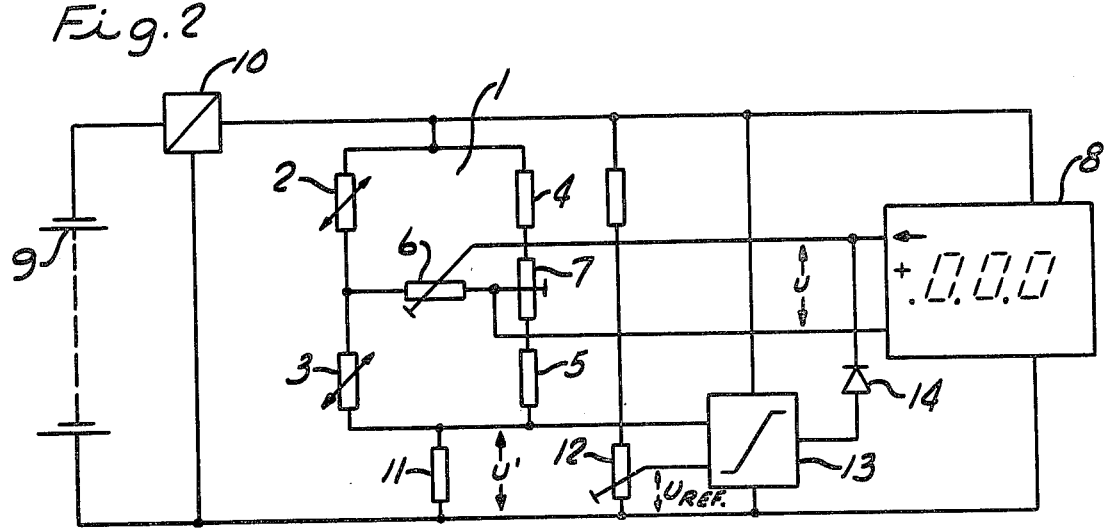

United States Patent [19]

Höht

[11] Patent Number: 4,476,096
[45] Date of Patent: Oct. 9, 1984

[54] CIRCUIT ARRANGEMENT FOR AN APPARATUS FOR MEASURING AND INDICATING THE CONCENTRATION OF COMBUSTIBLE GASES AND VAPORS CONTAINED IN AIR

[75] Inventor: Wolfgang Höht, Berlin, Fed. Rep. of Germany

[73] Assignee: Auergesellschaft GmbH, Berlin, Fed. Rep. of Germany

[21] Appl. No.: 407,120

[22] Filed: Aug. 11, 1982

[30] Foreign Application Priority Data

Aug. 12, 1981 [DE] Fed. Rep. of Germany ....... 3132297

[51] Int. Cl.³ .................. G01N 27/16; G01N 31/10
[52] U.S. Cl. .................. 422/96; 73/27 R; 340/633
[58] Field of Search ............ 422/96, 97; 436/151, 436/152; 73/27 R, 27 A; 340/633, 634

[56] References Cited

U.S. PATENT DOCUMENTS

| | | | |
|---|---|---|---|
| 2,285,280 | 6/1942 | Johnson | 422/96 X |
| 2,786,350 | 3/1957 | Johnson | 422/96 X |
| 3,237,181 | 2/1966 | Palmer | 340/633 |
| 3,497,323 | 2/1970 | Neubeit | 73/27 R |
| 3,519,391 | 7/1970 | Winter et al. | 436/152 |
| 4,074,243 | 2/1978 | Bogen et al. | 340/633 |
| 4,170,770 | 10/1979 | Ichinose et al. | 340/634 |
| 4,263,588 | 4/1981 | Gautier | 422/96 X |

Primary Examiner—Arnold Turk
Assistant Examiner—Robert J. Hill, Jr.
Attorney, Agent, or Firm—Carothers & Carothers

[57] ABSTRACT

Ambiguous measurement results can be obtained in the measurement and indication of high concentrations obtained in air of combustible gases when employing the thermal effect principle. In order to prevent such ambiguities from arising, the measuring range is, in accordance with the invention, limited to the linear part of the characteristic curve of the measuring sensor and displayed digitally.

1 Claim, 3 Drawing Figures

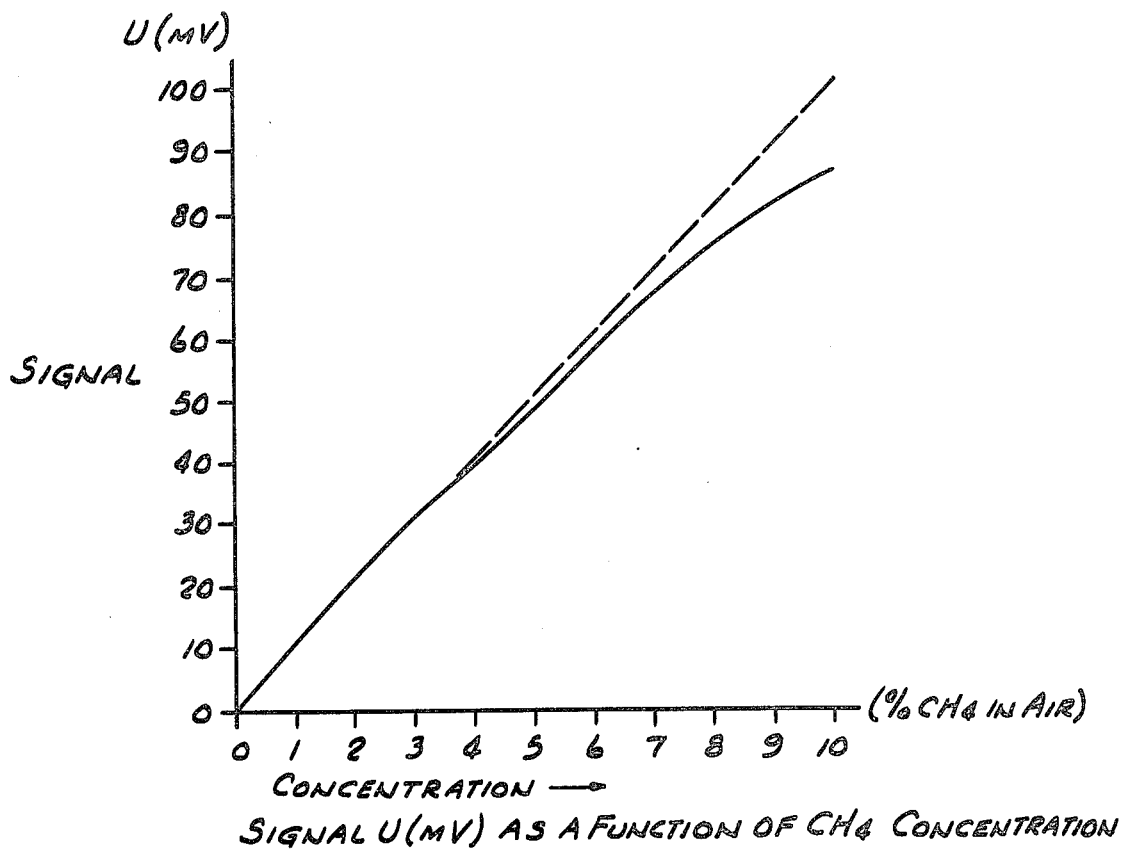
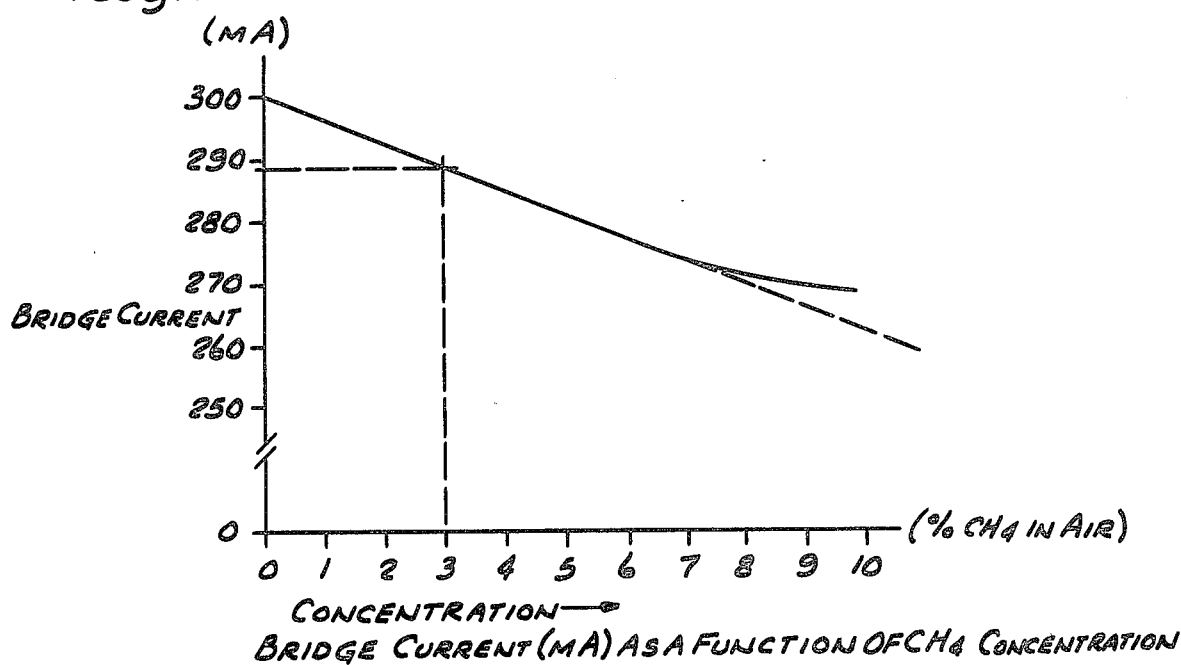

CIRCUIT ARRANGEMENT FOR AN APPARATUS FOR MEASURING AND INDICATING THE CONCENTRATION OF COMBUSTIBLE GASES AND VAPORS CONTAINED IN AIR

The invention pertains to a circuit arrangement which is used to measure and indicate the concentration of combustible gases and vapors contained in air.

When measurements are made of the fraction of combustible constituents in a gas-test using the thermal effect principle, the oxygen required for the combustion is insufficient at the higher gas concentrations. This can lead to ambiguous results because the indicating apparatus can indicate either a low or a high concentration.

This will be clear from the following example.

When, with the use of an apparatus made in accordance with the conception of the present invention, it is desired, for example, to determine the variation in the signal emitted by the measuring sensor and arriving at the indicator in order to measure the amount of methane, the concentration of methane in the sample to be measured is varied and the signals are plotted in a coordinate system as a function of the concentration, so that a curve is obtained as shown in FIG. 1. The curve clearly shows the non-linear variation of the signal U as a function of the methane concentration and, in fact, above 3 vol. % $CH_4$, the signal U is no longer proportional, with increasing $CH_4$—concentration, to the volume content. When using digital indicating apparatus, this behavior must be compensated in order to achieve the necessary indicating accuracy as, for example, by means of expensive measurement amplifiers with opposing amplification characteristics.

Proceeding from the assumption that, for making safety judgments in underground mining operations for example, a measuring range of 0 to 3 vol. % $CH_4$ is adequate, the basic task of the invention is the creation of a circuit arrangement for an apparatus to measure and indicate the concentration of combustible gases contained in air, the arrangement being such that the measuring range is restricted to the linear portion of the measuring sensor's characteristic curve and the measuring signal is fed digitally to the indicator.

This task is accomplished, in accordance with the invention, in conformity with the teaching presented in claim 1.

The advantages to be gained with the invention reside especially in the fact that a restriction of the measuring range is made possible by means of simple circuitry.

Additional advantageous embodiments of the invention are given in claims 2 to 4.

The appended figures illustrate, by way of example, an embodiment of the invention which is described in the following:

FIG. 2 schematically shows a basic circuit of a measuring arrangement with the measuring range limited in accordance with the invention, and FIG. 3 graphically presents a curve which shows the variation of the measuring-bridge current as a function of the concentration.

Arranged in a measuring bridge 1 are a catalytically active measuring sensor 2 which acts as a resistor for measurement, a catalytically inactive sensor 3 which acts as a comparison resistor, as well as resistors 4 and 5. Connected in the diagonal branch of the measuring bridge 1 is an adjusting resistor 6 for balancing the measuring signal voltage U and a potentiometer 7 for zero-balancing the measuring bridge, as well as a voltage measuring apparatus 8 which serves as an indicating instrument for indicating the measuring signal voltage U in digital form. The power supply to the measuring arrangement is provided by a primary or secondary battery 9 to which is series-connected a voltage stabilizer 10.

The circuit arrangement functions in the following way:

To indicate the signal voltage U, the voltage measuring apparatus (digital voltmeter) 8 is made in the form of a seven-segment indicator (LED or LCD) having a measuring range up to 99.9 mV, for example.

After zero-balancing the measuring bridge 1 by means of the potentiometer 7, a signal voltage of 10 mV/vol.% $CH_4$ is set by means of the adjusting resistor 6. By placing a decimal point after the first indicating element, it is possible, within the linear range, accurately to indicate the $CH_4$-concentration to two places after the decimal point, as, for example, 1.00 for 1 vol. % $CH_4$.

In order to limit the measuring range of the arrangement to the linear part of the catalytically active measuring sensor's characteristic curve, use is made of the cold-conductor (ptc-resistor) behavior of gas sensors.

For example, should a $CH_4$ concentration arrive at the catalytically active measuring sensor 2, the resistance of the sensor will increase as a result of the heat of combustion, with the result that, if the bridge voltage $U_{Br}$ is kept constant, the bridge current $I_{Br}$ will drop. The concentration-dependent change in bridge current is measured as a voltage drop U' across a resistor 11 and compared with a reference voltage $U_{ref}$. The reference voltage $U_{ref}$ represents a value above the concentration-dependent bridge voltage which is set on a voltage divider 12 and fed to a comparator 13. If the concentration-dependent voltage drop U' is greater than the reference voltage $U_{ref}$, the measured value does not influence the signal voltage U by the comparator 13. However, if $U' \leq U_{ref}$, the comparator 13 will then superimpose, via a diode 14, a positive voltage on the voltage U, the value of which is so proportioned that the measuring range of the digital indicator 8 is exceeded and the indication is blocked out. In other words, in addition to the concentration-dependent measuring signal U, above a switching point which is specified and set in the comparator 13, an additional signal is supplied by the comparator and superimposed on the measuring signal U in such a way that the measuring range of the digital indicating apparatus is definitely exceeded and the indication is blocked out.

Exceeding the measuring range of the indicator 8 can be signalled either by causing the indicating element to blink with the simultaneous lighting of the plus or minus sign, or by extinguishing the indicating elements with the simultaneous lighting-up of all the decimal points and of the plus sign, or by similar marked changes in the indication.

The restricting of the measuring range to the linear range of 0–3 vol. % $CH_4$, for example, is effected by adjusting the reference voltage $U_{ref}$ to a value which corresponds to a change in bridge current caused by a $CH_4$ concentration of 3 vol. %, the change in current being observed as a voltage U' across the resistor (see FIG. 3).

I claim:

1. In a circuit arrangement for an apparatus for the measurement and indication of the concentration of combustible gases and vapors contained in air by the thermal effect principle, including a bridge circuit for measurement of thermal effects produced during a combustion process of combustible gases and vapors and for producing a concentration-dependent measuring signal fed to an indicating apparatus, the bridge circuit having gas sensors in respective branches thereof which are in the form of a measuring sensor and a comparison sensor, and a comparator connected for transmitting an additional signal to the indicating apparatus at a specified measuring-bridge-voltage, the improvement comprising:

a. the comparator being connected in parallel with the measuring bridge and, via a diode means, in parallel to the indicating apparatus;
   b. a resistance connected in parallel with the comparator and connected in series with the bridge such that concentration-dependent bridge current is measured as a voltage drop across the resistance;
   c. the indicating apparatus being a digital indicating device, and
   d. a voltage divider connected to the comparator and adapted to provide a reference voltage which is fed to the comparator for comparison of said voltage drop with said voltage reference, said comparator adapted such that when the voltage drop attains or is less than the reference voltage an additional measuring signal is superimposed on the bridge-measuring signal such that the measuring range of the indicating device is exceeded whereby indication is switched off.

* * * * *